United States Patent [19]

De Keyzer et al.

[11] Patent Number: 4,859,565
[45] Date of Patent: Aug. 22, 1989

[54] DIFFUSION TRANSFER REVERSAL PROCESS

[75] Inventors: René M. De Keyzer, Bornem; Robert J. Pollet, Vremde; Leon L. Vermeulen, Herenthout, all of Belgium

[73] Assignee: Agfa-Gevaert, N.V., Mortsel, Belgium

[21] Appl. No.: 186,757

[22] Filed: Apr. 26, 1988

Related U.S. Application Data

[63] Continuation of Ser. No. 872,881, Jun. 1, 1986, abandoned.

[30] Foreign Application Priority Data

Jun. 11, 1985 [EP] European Pat. Off. ...... 85.200915.8

[51] Int. Cl.$^4$ .............................. G03C 5/54
[52] U.S. Cl. ........................ 430/231; 430/233; 430/234; 430/248; 430/251; 430/965
[58] Field of Search ............. 430/233, 248, 965, 251, 430/231, 611, 615

[56] References Cited

U.S. PATENT DOCUMENTS

| | | | |
|---|---|---|---|
| 2,852,375 | 9/1958 | Tinker | 430/615 |
| 3,017,270 | 1/1962 | Tregillos et al. | 430/248 |
| 3,053,657 | 9/1962 | Goodchild et al. | 430/233 |
| 3,600,171 | 8/1971 | Cole | 430/233 |
| 3,706,568 | 12/1972 | Haefner | 430/233 |
| 4,605,609 | 8/1986 | Okazaki et al. | 430/233 |
| 4,727,017 | 2/1988 | Pollet et al. | 430/611 |
| 4,728,601 | 3/1988 | Rowland et al. | 430/611 |

Primary Examiner—Richard L. Schilling
Attorney, Agent, or Firm—A. W. Breiner

[57] ABSTRACT

Method for making images by image-wise exposing a silver halide emulsion layer, developing it with an alkaline processing solution in the presence of a silver halide solvent, development nuclei, and a density- and tone-controlling compound, transferring silver complexes from the emulsion layer to a non-light-sensitive image-receiving layer and forming an image therein, said density- and tone-controlling compound being contained in said image-receiving layer and/or in said processing solution and corresponding to the general formula:

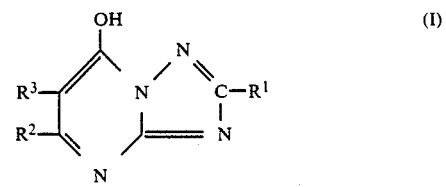

wherein $R^1$, $R^2$, and $R^3$ (same or different) represent hydrogen, $C_1$-$C_8$alkyl, or $Alk_1$—X—$Alk_2$—Y—; $Alk_1$ is (substituted) $C_1$-$C_8$alkyl; X is —O— or —S—; $Alk_2$ is (substituted) $C_1$-$C_8$alkylene; Y is a single bond, —O—, —S—, —CONH—, —SO$_2$NH—, or —NHCONH—; $R^3$ can alternatively represent (substituted) $C_1$-$C_8$alkylthio; at least one of $R^1$, $R^2$, and $R^3$ being other than hydrogen and other than $C_1$-$C_8$alkyl. The invention also provides an image-receiving layer and/or a processing solution incorporating such density- and tone-controlling compound.

7 Claims, No Drawings

DIFFUSION TRANSFER REVERSAL PROCESS

This application is a continuation of application Ser. No. 06/872,881, filed June 11, 1986, now abandoned.

DESCRIPTION

The present invention relates to the photographic silver complex diffusion transfer reversal process (DTR-process), in particular to a method for improving the density and the tone of images, produced according to the DTR-process, in the image-receiving layer and also relates to a non-light-sensitive element or a processing solution comprising density- and/or tone-controlling compounds.

The principles of the silver complex diffusion transfer reversal process, hereinafter called DTR-process, have been described e.g. in the U.S. Pat. No. 2,352,014.

In the DTR-process silver complexes are transferred by diffusion from a light-sensitive silver halide emulsion layer to an image-receiving layer, in which they are converted into a silver image by the action of development nuclei. For this purpose. an image-wise exposed silver halide emulsion layer is developed by means of a processsing solution in the presence of (a) developing agent(s) and a silver ion complexing agent, also called silver halide solvent. The silver halide in the exposed parts of a negative emulsion layer is developed to silver so that it cannot dissolve anymore and cosequently cannot diffuse. The silver halide in the unexposed parts of such negative emulsion layer is converted into soluble silver complexes by means of the silver halide solvent acting as a silver complexing agent. The soluble silver complexes are transferred by diffusion to an adjacent image-receiving layer or an image-receiving layer brought into effective contact with the emulsion layer, to form in the presence of development nuclei that catalyze the reduction of transferred complexed silver ions a positive silver image or silver-containing image in the receiving layer. When instead of a negative silver halide emulsion layer a direct-positive silver halide emulsion layer is used, the silver halide in the unexposed areas is developed and the silver halide in the exposed areas is transferred, as described hereinbefore, to form a negative silver image in the image-receiving layer. By "effective contact" is understood that dissolved silver salts can migrate by diffusion from the emulsion layer to the image-receiving layer, if desired, through an intermediate layer provided between this emulsion layer and this image-receiving layer. Whenever such intermediate layer is present, it must not impede the diffusion of the silver salts.

More details on the DTR-process can be found in "Photographic Silver Halide Diffusion Processes" by A. Rott and E. Weyde, Focal Press, London, New York (1972).

Unfortunately, the density of the image formed in the image-receiving layer is sometimes unsatisfactory and the image tone may often be unpleasant e.g. brownish.

Many attempts have therefore been made to improve the density and the tone of the resulting image.

For example, the U.S. Pat. No. 3,017,270 describes the use of certain quaternary ammonium or ternary sulphonium compounds. In the JP Pat. application Nos. 57/22,236 and 57/78,536 the use of certain quaternary imidazolinium or tetrahydropyridinium compounds is described. In the U.S. Pat. No. 4,310,613 the use of certain quaternary ammonium compounds is said to improve transmission density but likely to impair reflection density.

In the U.S. Pat. No. 3,053,657 the use of i.a. 5- and/or 6-alkyl-substituted 7-hydroxy-s-triazolo-[1,5-a]-pyrimidines is proposed for obtaining a blacker transfer image.

By the terms "transmission density" and "reflection density" as used herein are meant the diffuse transmission density and the diffuse reflection density respectively. The diffuse transmission density is measured according to the requirements of American Standard PH 2.19 -1959. The diffuse reflection density is measured according to the requirements of American Standard PH 2.17 - 1958.

Reflection density is influenced by the speed of transfer image formation. This speed of transfer image formation has an influence on the density build-up, on the speed of deposition of the image particles, on the concentration of the deposited image particles, on the depth of the deposition in the image-receiving layer, and on the form of the image particles. The density build-up of the image in the image-receiving layer should be such that incident light is not scattered by metallic particles at its surface so as to avoid any bronzing effect and thus to ensure a substantially neutral tone. In contrast, scattering of incident light by image particles that lie deeper in the transfer image must occur if the transfer image is to have a high reflection density. To promote interior rather than surface scattering the physical development of silver should be homogeneous within the layer. At the same time, the development must not substantially decrease the transmission density.

Many proposed compounds, although offering positive effects with respect to density and tone, are unacceptable in other respects. For instance, certain compounds have a tendency to cause formation of sludge. The quaternary ammonium salts described in the above-mentioned JP Patent application No. 57/78,536, even though they may improve the reflection density, can be synthesized only with great difficulty and as a consequence, they are hardly suitable from an economical standpoint. Moreover, they have a slight retarding effect on the diffusion transfer speed.

There thus remains a need to provide compounds that assist in the formation of high-quality images according to the DTR-process, in other words images having a high reflection density, but which compounds do not have any significant adverse side effects like that of retarding the diffusion transfer speed. At the same time, such compounds should be easily and economically synthesizable.

It has been found now that a class of substituted triazolopyrimidines can enhance the reflection density whilst not substantially decreasing the transmission density of transfer images formed by the DTR-process, at the same time improve the tone of such transfer images and do not retard the diffusion transfer speed. The compounds of this class can be prepared easily and economically.

The present invention provides a method of making a DTR-image comprising image-wise exposing a photosensitive element comprising a photographic silver halide emulsion layer, developing the exposed emulsion layer with the aid of an alkaline processing solution in the presence of a silver halide solvent and causing silver complexes to diffuse from the emulsion layer into a non-light-sensitive image-receiving layer in the presence of development nuclei thereby to form a silver transfer image in that layer, said transfer image formation occurring in the presence of at least one 7-hydroxy-s-triazolo-[1,5-a]-pyrimidine, which influences the density and tone of said transfer image, characterized in that said 7-hydroxy-s-triazolo-[1,5-a]-pyrimidine is contained in said non-light-sensitive image-receiving layer or a non-light-sensitive hydrophilic colloid layer in water-permeable relationship therewith and/or in said alkaline processing solution and corresponds to the following general formula (I):

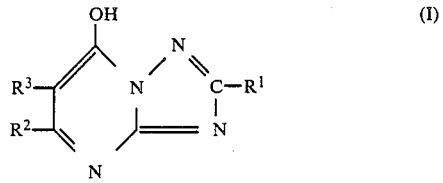

wherein:
  each $R^1$, $R^2$, and $R^3$, which may be the same or different, represents:
  (a) hydrogen
  (b) a $C_1$-$C_8$alkyl group, e.g. methyl, or
  (c) an $Alk_1$ - X- $Alk_2$ -Y-group,
  wherein
    $Alk_1$ represents a $C_1$-$C_8$alkyl group e.g. methyl, ethyl, or octyl, or a substituted $C_1$-$C_8$alkyl group e.g. $C_1$-$C_8$alkyl substituted with hydroxy, carboxy, acetoxy, phenyl, $C_1$-$C_8$alkylthio such as methylthio or ethylthio, $C_1$-$C_8$alkythio such as methoxy, hydroxy-$C_1$-$C_8$alkyl thio such as 2-hydroxyethylthio, or hydroxy-$C_1$-$C_8$alkyloxy,
    X represents —O— or —S—,
    $Alk_2$ represents a $C_1$-$C_8$alkylene group e.g. methylene or ethylene, or a substituted $C_1$-$C_8$alkylene group e.g. $C_1$-$C_8$alkylene substituted with carboxy or carboxymethyl, and
    Y represents a single bond, —O—, —S—, —CONH—, —$SO_2$NH—, or —NHCONH—,
  or wherein:
    each of $R^1$ and $R^2$ (the same or different) represents hydrogen or a said group (b) or (c) and $R^3$ represents a thio group or a $C_1$-$C_8$alkylthio group, the group of which is substituted e.g. with hydroxy, carboxy, acetoxy, phenyl, kylthio, $C_1$-$C^8$alkyloxy, hydroxy-$C_1$-$C_8$alkylthio, or hydroxy-$C_1$-$C_8$alkyloxy,
  at least one of $R^1$, $R^2$, and $R^3$, however, being other than hydrogen and other than $C_1$-$C_8$alkyl.

The present invention also provides a non-light-sensitive element comprising an image-receiving layer incorporating at least one 7-hydroxy-s-triazolo-[1,5-a]-pyrimidine corresponding to the above general formula (I).

The present invention also provides a processing solution comprising at least one 7-hydroxy-s-triazolo-[1,5-a ]-pyrimidine corresponding to the above general formula (I).

It has been established that the 7-hydroxy-s-triazolo-[1,5-a]-pyrimidines corresponding to the above general formula (I). wnen present in effective amounts in the non-light-sensitive image-receiving layer and/or in the alkaline processing solution during the diffusion transfer, enhance the diffusibility of the silver complexes, in consequence of which the latter tend to diffuse deeper into the image-receiving layer before forming the diffusion transfer image. As a consequence, the internal and external light scattering by the transfer image particles reach a balance that results in an advantageous, low reflection, which greatly adds to the appreciability of the density and/or tone of the positive image.

In accordance with the present invention at least one 7-hydroxy-s-triazolo-[1,5-a]-pyrimidine corresponding to the above general formula (I) is incorporated in the element containing the non-light-sensitive image-receiving layer and/or is added to the processing solution.

Representatives of 7-hydroxy-s-triazolo-[1,5-a]-pyrimidine compounds corresponding to the above general formula (I) that can be used in accordance with the present invention are listed in the following Table 1, the symbols used therein referring to the above general formula (I).

TABLE 1

| Compound | $R^1$ | $R^2$ | $R^3$ |
|---|---|---|---|
| 1 | —$CH_2$—O—$CH_3$ | —$CH_3$ | —H |
| 2 | —$CH_2$—S—$CH_3$ | —$CH_3$ | —H |
| 3 | —$CH_2$—S—$(CH_2)_7$—$CH_3$ | —$CH_3$ | —H |
| 4 | —$CH_2$—S—$CH_2$COOH | —$CH_3$ | —H |
| 5 | —$CH_2$—S—$CH_2CH_2OH$ | —$CH_3$ | —H |
| 6 | —$CH_2$—S—$CH_2CH_2$—S—$C_2H_5$ | —$CH_3$ | —H |
| 7 | —$CH_2$—S—$CH_2CH_2$—S—$CH_2CH_2OH$ | —$CH_3$ | —H |
| 8 | —$CH_2$—S—$CH_2$—$C_6H_5$ | —$CH_3$ | —H |
| 9 | —$CH_2CH_2$—S—$CH_3$ | —$CH_3$ | —H |
| 10 | —S—$CH_2CH_2$—S—$C_2H_5$ | —$CH_3$ | —H |
| 11 | —S—$CH_2CH_2$—S—$CH_2CH_2OH$ | —$CH_3$ | —H |
| 12 | —NHCO—$CH_2$—S—$CH_3$ | —$CH_3$ | —H |
| 13 | —NHCO—$CH_2$—O—$CH_3$ | —$CH_3$ | —H |
| 14 | —H | —$CH_2$—O—$CH_3$ | —H |
| 15 | —H | —$CH_2$—S—$CH_3$ | —H |
| 16 | —H | —$CH_2$—S—$CH_2$COOH | —H |
| 17 | —H | —$CH_2$—S—$CH_2CH_2$O—CO—$CH_3$ | —H |
| 18 | —H | —$CH_2$—S—$CH_2CH_2OH$ | —H |
| 19 | —H | —$CH_2$—S—$CH_2$—$C_6H_5$ | —H |
| 20 | —H | —$CH_2$—S—$CH_2CH_2$—S—$C_2H_5$ | —H |
| 21 | —$CH_2$—S—$CH_3$ | —$CH_2$—S—$CH_3$ | —H |
| 22 | —H | —$CH_3$ | —S—$CH_2$—$C_6H_5$ |
| 23 | —H | —$CH_3$ | —S—$CH_2$—COOH |
| 24 | —H | —$CH_3$ | —S—$CH_2$—$CH_2$O—CO—$CH_3$ |
| 25 | —H | —$CH_3$ | —S—$CH_2$—$CH_2OH$ |
| 26 | —H | —$CH_3$ | —S—$CH_2$—CHOH—$CH_2OH$ |
| 27 | —H | —$CH_3$ | —S—$CH_2$—$CH_2$—S—$CH_2$—$CH_2OH$ |
| 28 | —H | —$CH_3$ | —$CH_2$—S—$CH_3$ |
| 29 | —H | —$CH_3$ | —$CH_2$—S—$CH_2$—COOH |

TABLE 1-continued

| Compound | R¹ | R² | R³ |
|---|---|---|---|
| 30 | —H | —CH₃ | —CH₂—S—CH₂—CH₂OH |
| 31 | —H | —CH₃ | —NHCO—CH₂—S—CH₃ |
| 32 | —H | —CH₃ | —NHCO—CH₂—S—CH₂—COOH |
| 33 | —H | —CH₃ | —NHCO—CH—S—(CH₂)₃—CH₃<br>             \|<br>            CH₂—COOH |
| 34 | —H | —CH₃ | —NHCO—CH₂—O—CH₃ |
| 35 | —H | —CH₃ | —NHCO—CH₂—O—CH₂—COOH |
| 36 | —H | —CH₂—S—CH₂CH₂COOH | —H |
| 37 | —H | —CH₂—S—CH₂CH₂—COOCH₃ | —H |

The 7-hydroxy-s-triazolo-[1,5-a]-pyrimidine compounds corresponding to the above general formula (I) can prepared by techniques described by G. Fischer in Journal für Signalaufzeichnungsmaterialien 1, 33–42 (1973). For instance. they can be prepared by condensation of a Beta-keto-ester or of a substituted Beta-keto-ester with a 5-amino-1,2,4-triazole according to the following reaction scheme:

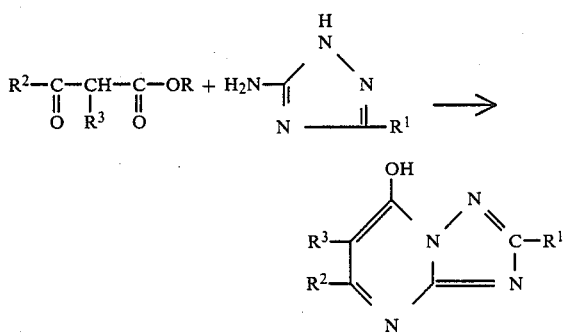

They can also be prepared by conversion of appropriate substituents such as e.g. a mercapto group or an amino group standing on the 2-, 5-, and/or 6-position of a 7-hydroxy-s-triazolo-[1,5-a]-pyrimidine ring system into the specific R¹, R², and/or R³ substituents of the compounds corresponding to the above general formula (I).

The compounds of the invention can be prepared very simply and very economically by the foregoing methods.

A description of the synthesis of some of the compounds identified in Table 1 is given hereinafter by way of example. The synthesis of other compounds identified in Table 1 as well as of compounds not identified in Table 1 but corresponding to the above general formula (I) can easily be derived from the syntheses described hereinafter.

Preparation 1

Compound 1

An amount of 21.8 g (0.17 mol) of 3-methoxymethyl-5-amino-1,2,4-triazole melting at 100° C. and 32.5 g (0.28 mol) of methyl acetoacetate was refluxed for 4 h in 50 ml of acetic acid. A mixture consisting of methanol, water, and acetic acid (25 ml) was distilled off. The remaining reaction action mixture was stirred with 50 ml of ethanol, filtered with suction, and rinsed with ethanol.

Yield: 11.5 g (35%) of Compound 1. Melting point: above 265° C.

Preparation 2

Compound 2

Compound 2 was prepared analogously to Compound 1 as described above, but from 3-methylthiomethyl-5-amino-1,2,4-triazole melting at 125° C. and methyl acetoacetate in acetic acid.

Yield: (42%).

Melting point: 243° C.

Preparation 3

Compound 4

(a) 2-Mercaptomethyl-5-methyl-7-hydroxy-s-triazolo-[1.5-a]-pyrimidine was prepared by first hydrolysing the corresponding thiouronium salt, as described in the U.S. Pat. No. 2,835,581, in boiling aqueous sodium hydroxide under nitrogen atmosphere and then acidifying.

Yield: (75%). Melting point: 215° C.

(b) A solution of 23.3 g (0.2 mol) of the sodium salt of chloroacetic acid in 150 ml of water was added dropwise under nitrogen atmosphere to a solution of 39.2 g (0.2 mol) of compound (a), prepared as described above, in 80 ml (0.4 mol) of 5N sodium hydroxide. After having been stirred for 6 h at room temperature, the reaction mixture was filtered. The filtrate was acidified with concentrated hydrochloric acid. The precipitate was filtered with suction and rinsed with water and methanol.

Yield: 37.5 g (74%) of 2-carboxymethylthiomethyl-5-methyl-7-hydroxy-s-triazolo-[1,5-a]-pyrimidine (Compound 4). Melting point: above 265° C.

Preparation 4

Compound 6

17.4 g (0.08 mol) of 3-[2-(ethylthio) -ethylthiomethyll-]-5-amino-1 2,4-triazole melting at about 80° C. and 13.9 g (0.12 mol) of methyl acetoacetate were refluxed for 4 h in 30 ml of acetic acid. The precipitate was filtered with suction and rinsed with ethanol.

Yield: 13.5 g (59%) of Compound 6. Melting point: about 165° C.

Preparation 5

Compound 9

Compound 9 was prepared analogously to Compound 1 as described above, but from 3-[2-(methylthio)-ethyl]-5-amino-1,2,4-triazole melting at about 110° C. and methyl acetoacetate in acetic acid.

Yield: (69%). Melting point: 222° C.

Preparation 6

Compound 10

Compound 10 was prepared analogously to Compound 1.

Yield: (30%). Melting point: 168° C.

Preparation 7

Compound 14

Compound 14 was prepared analogously to Compound 1 as described above, but from ethyl 4-methoxyacetoacetate boiling at 55°–60° C./5 mm and prepared as described in Journal of Organic Chemistry 43, 2087 (1978).

Yield (75%). Melting point: about 265° C.

Preparation 8

Compound 15

Compound 15 was prepared analogously to Compound 6 as described above, but from 4-(methylthio)acetoacetic acid methyl ester boiling at 78°–79° C./1.5 mm.

Yield: (73%). Melting point: 215° C.

Preparation 17

Compound 17

Compound 17 was prepared analogously to Compound 1 as described above, but from 4-(2-acetoxy-ethyl-thio)acetoacetic acid methyl ester boiling at 129°–131° C./0.5 mm and prepared by alkylation of 2-acetoxy-ethanethiol with 4-chloro-acetoacetic acid methyl ester in a mixture of toluene and triethylamine.

Yield: (85%). Melting point: about 120° C.

Preparation 10

Compound 18

12.5 ml of concentrated hydrochloric acid was added dropwise to a solution of 26.8 g (0.1 mol) of Compound 17 in 100 ml of methanol. The reaction mixture was refluxed for 5 h. The precipitate was filtered with suction and recrystallized from water.

Yield: 11.5 g of Compound 18 (51%). Melting point: 199° C.

Preparation 11

Compound 20

Compound 20 was prepared analogously to Compound 6 as described above, but from 4-[2-(ethylthio)-ethylthio]-acetoacetic acid ethyl ester boiling at 140°–145° C./1 mm.

Yield: (25%). Melting point: about 170° C.

Preparation 12

Compound 21

15.3 g (0.1 mol) of 3-methylthiomethyl-5-amino-1,2,4-triazole and 16.2 g (0.1 mol) of 4-(methylthio)-acetoacetic acid methyl ester in 15 ml of acetic acid were refluxed for 24 h. The reaction product was concentrated by evaporation and purified by column chromatography.

Yield: 10 g (39%) of Compound 21. Melting point: 158° C.

Preparation 13

Compound 24

Compound 24 was prepared analogously to Compound 1 as described above, but from 2-(acetoxy-ethylthio)-acetoacetic acid ethyl ester boiling at 108°–110° C./0.5 mm and prepared by alkylation of 2-acetoxy-ethanethiol with 2-chloroacetoacetic acid ethyl ester in a mixture of toluene and triethylamine.

Yield: (77%). Melting point: about 100° C.

Preparation 14

Compound 25

Compound 25 was prepared analogously to Compound 18 as described above, but from Compound 24 as described above.

Yield: (67%). Melting point: about 210° C.

Preparation 15

Compound 30

15.4 g (0.05 mol) of 5-methyl-6-diethylaminomethyl-7-hydroxy-s-triazolo-[1,5-a]-pyrimidine prepared as described in the U.S. Pat. No. 3,563,755 and 3.9 g (0.05 mol) of 2-mercapto-ethanol in 50 ml of dimethylformamide were heated for 16 h at 120° C. After filtration the reaction mixture was concentrated by evaporation. The residue was dissolved in 50 ml of water and acidified with concentrated hydrochloric acid. The precipitate was filtered with suction and rinsed with ethanol.

Yield: 6.5 g (54%) of Compound 30. Melting point: 170° C.

Preparation 16

Compound 31

12.4 g (0.1 mol) of methylthioacetyl chloride was added dropwise to 18.7 g (0.1 mol) of the sodium salt of 5-methyl-6-amino-7-hydroxy-s-triazolo-[1,5-a]-pyrimidine prepared as described in Chemical Abstracts 59, 1659e (1963) and 7.9 g (0.1 mol) of pyridine in 150 ml of anhydrous dioxan. The precipitate was filtered with suction, rinsed with dioxan, and purified by continuous extraction with methanol.

Yield: 10 g (40%) of Compound 31. Melting point: about 230° C.

In order to make possible a rapid formation of silver complexes with the aid of the silver halide solvent, the silver halide of the photographic silver halide emulsion of the photosensitive element used in accordance with the present invention preferably consists of at least 70 mole % of silver chloride, the remainder being preferably silver bromide. The average silver halide grain size can e.g. be in the range of 200–300 nm.

A suitable coverage of silver halide expressed in g of silver nitrate per m$^2$ is in the range of 1 to 5 g/m$^2$.

The binder of the photographic silver halide emulsion layer preferably is gelatin. But instead of or together with gelatin, use can be made of one or more other natural and/or synthetic hydrophilic colloids e.g. albumin, casein, zein, polyvinyl alcohol, alginic acids or salts thereof, cellulose derivatives such as carboxymethyl cellulose, modified gelatin, etc. The weight ratio of hydrophilic colloid to silver halide expressed as equivalent amount of silver nitrate in the silver halide emulsion layer(s) of the photosensitive element can e.g. be between 1:1 and 10:1.

In addition to the binder and the silver halide, the photosensitive element may contain in the photographic silver halide emulsion layer and/or in one or more layers in water-permeable relationship therewith any of the kinds of compounds customarily used in such layers for carrying out the DTR-process. Such layers may comprise e.g. one or more developing agents, coating aids, stabilizing agents or fog-inhibiting agents e.g. as described in the GB Pat. specification No. 1,007,020 filed Mar. 6, 1963 by Agfa A.G., plasticizers, spectral sensitizing agents, development-influencing agents e.g. polyoxyalkylene compounds, onium compounds, and thioether compounds as decribed in the U.S. Pat. Nos. 2,938,792; 3,021,215; 3,038,805; 3,046,134; 4,013,471; 4,072,523; 4,072,523; 4,072,526; 4,292,400, and in the DE Pat. specification No. 1,124,354, hardeners, spectral sensitizing agents, etc.

A suitable spectral sensitizing agent for use in the photographic silver halide emulsion layer is the compound corresponding to the following structural formula II:

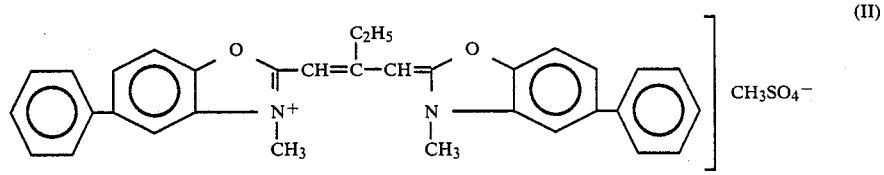

Other interesting spectral sensitizing agents for use in photographic silver chloride emulsions that have an average grain size higher than 0.5 micrometer and that have been hardened by means of formaldehyde are the compounds corresponding to the following structural formulae III and IV:

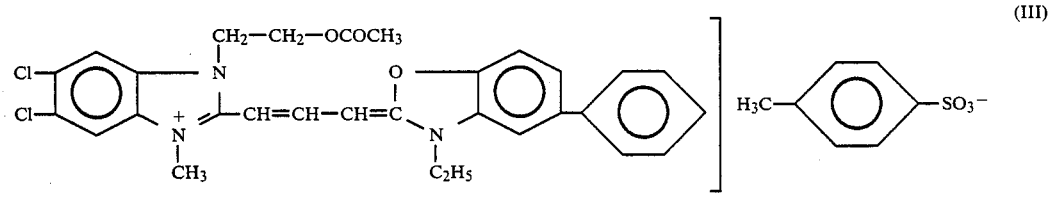

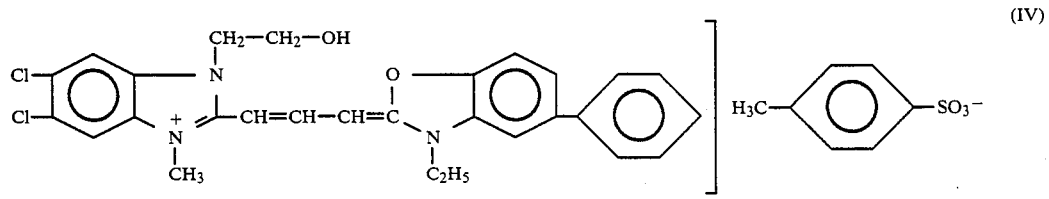

With respect to the hardening of photographic hydrophilic colloid silver halide emulsions it has been established that vinylsulphonyl compounds described in, e.g. DE-OS No. 2,749,260, DE Pat. specification No. 1,808,685, DE-OS No. 2,348,194 and Research Disclosure No. 22,507 of January 1983, e.g. vinylsulphonyl compounds of the formula $(CH_2=CH-SO_2)_2-R$, wherein R is $-CH_2-CH_2-O-CH_2-CH_2-$, $-(CH_2)_n-$ with n is 1 to 6 or $CH_3O(CH_2)_2-CH=$, unexpectedly also have a hardening effect when present in acid coating conditions of said emulsions.

The support of the photosensitive element used in accordance with the present invention can be of any of the support materials customarily employed in the art. They include paper, glass or film, e.g. cellulose acetate film, polyvinyl acetal film, polystyrene film, polyethylene terephthalate film etc. as well as metal supports and metal supports laminated on both sides with paper. Paper supports coated on one or both sides with an Alpha-olefin polymer, e.g. polyethylene, are used preferably. In order to compensate for the curling tendency of the photosensitive element, one side of its support can be coated with a polyethylene layer, whose specific density and/or thickness differ from those measured at the other side of the support. This compensation for the curling tendency can be improved by application of a hydrophilic colloid anti-curling layer optionally incorporating matting agents.

The emulsion-coated side of the photosensitive element can be provided with a top layer that contains water-permeable colloids. Such top layer will usually be free of gelatin. It must be of such nature that the diffusion is not inhibited or restrained. Such layer may act e.g. as an antistress layer. Appropriate water-permeable binding agents for a layer coated on top of the photographic silver halide emulsion layer are e.g. methyl cellulose, the sodium salt of carboxymethyl cellulose, hydroxyethyl cellulose, hydroxyethyl starch, hydroxypropyl starch, sodium alginate, gum tragacanth, starch, polyvinyl alcohol, polyacrylic acid, polyacrylamide, polyvinyl pyrrolidone, polyoxyethylene, copoly(methylvinylether/maleic acid), etc. The thickness of this layer depends on the nature of the colloid used. Such layer, if present, may be transferred at least partially to the image-receiving layer when the DTR-process comes to an end.

The silver halide emulsion of the photosensitive element used in accordance with the present invention is prepared in a known way by precipitation reaction of halides, e.g. ammonium halide, potassium, sodium, lithium, cadmium and strontium halide with silver salts, e.g. silver nitrate, in a hydrophilic protective binder, preferably gelatin. In case developing agents are to be incorporated into the silver halide emulsion, they are added to the emulsion composition preferably after the chemical ripening stage following the washing of the emulsion.

The DTR-image can be formed in the image-receiving layer of a so-called single-support-element, also called "mono-sheet" element, which contains the photographic silver halide emulsion layer(s) and the image-receiving layer in water-permeable relationship, e.g. on top of each other, or the DTR-image can be formed in an image-receiving layer of a separate element, which is brought into contact with the photosensitive element preparatory to the silver complex diffusion.

Examples of "mono-sheet" elements comprising a light-shielding pigment layer have been described in the DE Pat. specification No. 1,772,603 and the U.S. Pat. Nos. 3,629,054 and 3,928,037.

In the case of a separately supported image-receiving layer this layer can be coated on an opaque or transparent support, which can be one of the supports described hereinbefore for the photosensitive element.

It is also possible to obtain at least two transfer images from one silver halide emulsion during only one single imbibition step by the combined use of a mono-sheet element and a second element comprising a separately supported image-receiving layer. In that case the mono-sheet element may consist of a layer pack comprising in the given order: a transparent film support e.g. a polyethylene terephthalate support, an image-receiving layer, a light-shielding pigment layer e.g. a layer containing titanium oxide, and a silver halide emulsion layer e.g. a negative-working silver halide emulsion layer, whereas the second element may comprise a transparent film support e.g. a polyethylene terephthalate support, and an image-receiving layer. For anti-curling purposes as well as for convenience the film support may carry an image-receiving layer on either side. It is self-evident that the mono-sheet element as well the second element may comprise other conventional layers e.g. subbing layers.

The image-receiving layer or a layer adjacent thereto and in water-permeable relationship therewith may contain one or more agents for promoting the reduction of the diffusing silver complexes into metallic silver, these agents being called development nuclei. Such development nuclei have been described in the above-mentioned book by A. Rott and E. Heyde on pages 54–57. Suitable development nuclei are e.g. colloidal silver, heavy metal sulphides e.g. cobalt sulphide, zinc sulphide, nickel sulphide, silver nickel sulphide. A preferred type of development nuclei are silver nickel sulphide nuclei. The development nuclei can also be incorporated into the processing liquid as described in GB Pat. specification No. 1,001,558, filed April 13, 1962 by Gevaert Photo-Producten N.V.

The 7-hydroxy-s-triazolo-[1,5-a]-pyrimidine compounds corresponding to the above general formula (I) can be incorporated into the non-light-sensitive image-receiving layer in amounts of 1 mg to 200 mg per m². Preferably, they are incorporated into the non-light-sensitive image-receiving layer in amounts of 10 mg to 100 mg per m². They can also be incorporated in equivalent operative amounts into a non-light-sensitive hydrophilic colloid layer that is in water-permeable relationship with the image-receiving layer.

In one or more layers of the non-light-sensitive element comprising an image-receiving layer, other substances can also be incorporated, which play a contributory part in the formation of the diffusion transfer images. Such substances include black-toning agents, e.g. those described in GB Pat. specification No. 561,875, filed Dec. 3, 1942 by Ilford Ltd. and in BE Pat. specification No. 502,525 filed Apr. 12, 1951 by Agfa A.G. A preferred black-toning agent is 1-phenyl-5-mercaptotetrazole.

The image-receiving layer may consist of or comprise any of the binders mentioned hereinbefore for the silver halide, gelatin being the preferred binder for the image-receiving layer.

The non-light-sensitive element may in the image-receiving layer or in a hydrophilic colloid layer in water-permeable relationship therewith comprise a silver halide solvent. e.g. sodium thiosulphate in an amount of approximately 0.1 g to approximately 4 g per m².

The non-light-sensitive element may in the image-receiving layer or in a hydrophilic colloid layer in water-permeable relationship therewith comprise colloidal silica.

The image-receiving layer may have been hardened to achieve enhanced mechanical strength. Appropriate hardening agents for hardening the natural and/or synthetic hydrophilic colloid binding agents in the image-receiving layer include e.g. formaldehyde, glyoxal, mucochloric acid, and chrome alum. Hardening can also be effected by incorporating a hardener precursor in the image-receiving layer, the hardening of the hydrophilic colloid therein being triggered by the treatment with the alkaline processing liquid.

A suitable hardening agent is a triazine compound having the following structural formula V:

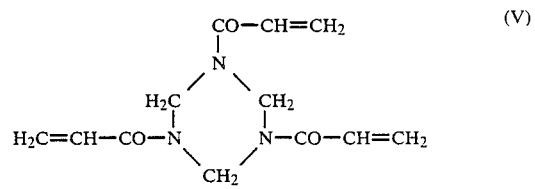

Other suitable hardening agents for hardening the hydrophilic colloid binding agents in the image-receiving layer are vinylsulphonyl hardeners such as those described hereinbefore for the hardening of photographic hydrophilic colloid silver halide emulsions.

The image-receiving layer may also comprise plasticizers, optical brighteners, and substances improving its adherence to the support.

A suitable plasticizing binding agent includes repeating units x, y and z as represented in the following general formula VI:

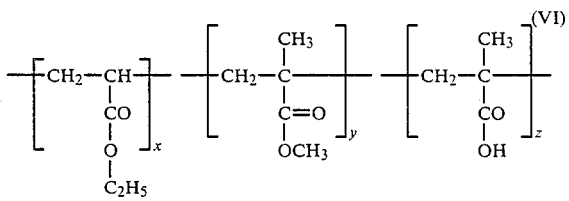

A suitable optical brightening agent has the following structural formula VII:

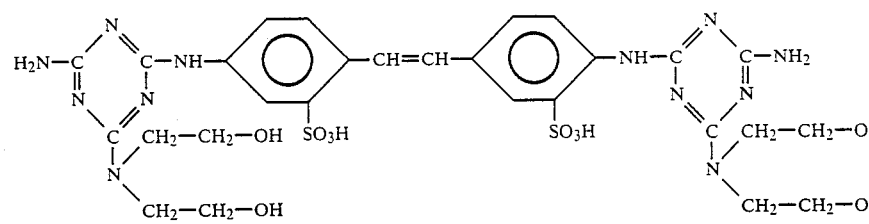

The adherence to resin film supports or paper supports of layers containing colloidal silica (SiO$_2$) can be improved with epoxysilane compounds, e.g. a compound having the following structural formula VIII:

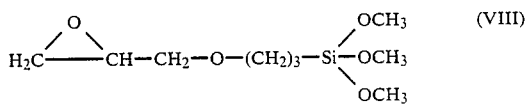

For instance the adherence of an image-receiving layer to a film or paper support can be improved considerably by the presence in such image-receiving layer of a combination of colloidal silica and an above-mentioned epoxysilane. A preferred combination is that of silica and the epoxysilane corresponding to formula VIII. This specific combination is called SiO$_2$/epoxysilane hereinafter. The adherence can also be improved with a dihydroxybenzene e.g. resorcinol and/or with succinimide. The adherence can be further improved by combining colloidal silica. an epoxysilane, a dihydroxybenzene, and succinimide in the image-receiving layer.

It is also found surprisingly that, when at least one of the group consisting of the combination of colloidal silica SiO$_2$-/epoxysilane combination, a dihydroxybenzene, and succinimide was incorporated into the image-receiving layer and/or into a hydrophilic colloid covering layer coated thereon and in water-permeable relationship therewith, the reflection density of the image obtained was enhanced. An even more enhanced reflection density can be achieved advantageously by combining the use of at least one density- and tone-controlling compound in accordance with the present invention with the use of at least one of the group consisting of the combination of colloidal silica and an epoxysilane e.g. the above-mentioned SiO$_2$/epoxysilane combination, a dihydroxybenzene, and succinimide in the image-receiving layer and/or in a hydrophilic colloid covering layer coated thereon and in water-permeable relationship therewith.

Furthermore, the combination of colloidal silica (SiO$_2$) with epoxysilane compounds, e.g. the compound having the above structural formula VIII also offers a very interesting non-diffusing hardener composition for use in hydrophilic colloid covering layers or antistress layers of photographic silver halide emulsion layers.

The non-light-sensitive element may, in the image-receiving layer in operative contact with the developing nuclei, contain thioether compounds such as those described in GE Pat. specification No. 1,124,354, in U.S. Pat. Nos. 4,013,471 and 4,072,526, and in the published EU Pat. application No. 0,026,520.

The non-light-sensitive element comprising an image-receiving layer may be provided with printing matter, e.g. with any type of recognition data applied by any type of conventional printing process such as offset printing, intaglio printing, etc.

For further information relevant to the composition of the image-receiving layer there can be referred to the above-mentioned book by Andre Rott and Edith Weyde p. 50–65.

Preferred image-receiving layer compositions for use in accordance with the present invention comprise gelatin as binding agent, silver nickel sulphide development nuclei, and at least one 7-hydroxy-s-triazolo-[1,5-a]-pyrimidine compound corresponding to the above general formula (I).

The processing solution for effecting the development of the exposed silver halide in the emulsion layer of the photosensitive element and the diffusion transfer of the silver complexes to the non-light-sensitive element is an alkaline solution.

The 7-hydroxy-s-triazolo-[1,5-a]-pyrimidine compounds corresponding to the above general formula (I) can be added to the akaline processing solution in amounts of 5 mg to 500 mg per liter. Preferably, they are added thereto in amounts of 10 mg to 100 mg per liter.

The developing agent or a mixture of developing agents can be incorporated into the alkaline processing solution and/or into the photosensitive element comprising a photographic silver halide emulsion layer and/or into the non-light-sensitive element comprising an image-receiving layer. When incorporated into the photosensitive element, the developing agent(s) can be present in the silver halide emulsion layer but such agent(s) is (are) preferably present in a hydrophilic colloid layer in water-permeable relationship therewith, e.g. in an anti-halation layer adjacent to the silver halide emulsion layer of the photosensitive element. When incorporated into the non-light-sensitive element comprising an image-receiving layer, the developing agent(s) can be present in the image-receiving layer or in a hydrophilic colloid layer in water-permeable relationship therewith. In case the developing agent or a mixture of developing agents is contained in the photosensitive element and/or in the non-light-sensitive element, the processing solution is merely an aqueous alkaline solution that initiates and activates the development.

Suitable developing agents for the exposed silver halide are e.g. hydroquinone-type and 1-phenyl-3-pyrazolidinone-type developing agents as well as p-monomethylaminophenol.

The silver halide solvent, preferably sodium thiosulphate, can be incorporated into the non-light-sensitive element as mentioned above, but also integrally or partly into the alkaline processing solution. When present in the alkaline processing solution, the amount of silver halide solvent is in the range of e.g. 10 g/l to 50 g/l.

The alkaline processing solution usually contains alkaline substances such as tribasic phosphate, preserving agents e.g. sodium sulphite, thickening agents e.g. hydroxyethylcellulose and carboxymethylcellulose, fog-inhibiting agents such as potassium bromide, silver halide solvents e.g. sodium or ammonium thiosulphate, black-toning agents especially heterocyclic mercapto compounds e.g. 1-phenyl-5-mercaptotetrazole. The pH of the processing solution is preferably in the range of 10 to 14.

With respect to alkaline substances for use in the alkaline processing solution, combinations of sodium carbonate with sodium hydroxide and/or 2-methylamino-ethanol were found to be advantageous because of improved buffering action and retarded exhaustion of the processing solution.

For particulars about exposure and developing apparatus, which may be applied in the DTR-process according to the present invention reference is made e.g. to "Photographic Silver Halide Diffusion Processes" by A. Rott and E. Weyde, Focal Press London, New York 1972 and to patent literature cited therein.

The photographic elements for use in accordance with the present invention can be used in the form of roll film or sheet film or in the form of a filmpack e.g., for in-camera-processing.

The photographic elements used in accordance with the present invention can also be destined for the production of identification documents according to the DTR-process. Such identification documents contain a photograph and/or identification data formed by diffusion transfer in an image-receiving layer on a polyethylene-covered paper support, which to exclude any forgery by alteration of the identification data and/or photograph, is laminated to a transparent protective cover sheet. The transparent protective cover sheet usually is a thermoplastic resin sheet such as a polyester film sheet, e.g. a polyethylene terephtalate film sheet, which is coated with polyethylene at the side that is to be laminated against the image-receiving-layer carrying the identification data. It has been experienced unfortunately that the unwinding of such polyethylene-coated polyester film sheet, when in wound up condition on reels, is rather difficult because the rear polyester side of the film sheet tends to stick to the opposite polyethylene-coated side. To avoid this disturbing sticking the rear polyester side of the film sheet can be coated with a very thin antisticking layer prior to the application of the polyethylene coating to the front side and before the transverse stretching of the polyester film sheet.

The following examples illustrate the present invention. The ratios and percentages given therein are by weight unless otherwise stated. The compound numbers used in these examples denote the compounds identified by those numbers in Table 1 herein.

EXAMPLE 1

A gelatin silver chloride emulsion (gelatin/silver nitrate = 1.67). hardened in the usual way with formaldehyde, was coated at 45° C. on a polyethylene-covered paper support of 140 g per m² in such a way that an amount of silver chloride equivalent to 0.6 g of silver nitrate is present per m².

The dry emulsion layer was covered with the following top layer composition at a ratio of 1 l per 20 m² and a temperature of 45° C:

| | |
|---|---|
| demineralized water | 800 ml |
| hydroxyethyl starch having a substitution degree | |
| of 0.27 hydroxyethyl groups | 40 g |
| ethanol | 200 ml |
| 1-phenyl-3-pyrazolidone | 5 g |
| hydroquinone | 10 g |
| 20% aqueous formaldehyde | 10 ml |

The resulting photosensitive element was image-wise exposed and then moistened, at the emulsion side only, with the following processing solution:

| | |
|---|---|
| demineralized water | 1000 ml |
| sodium phosphate | 75 g |
| anhydrous sodium sulphite | 40 g |
| anhydrous sodium thiosulphate | 40 g |

After 3 to 5 s the moistened photosensitive element was brought in contact for 8 s with the image-receiving layer of a non-light-sensitive element, prepared by coating a paper support of 110 g/m² on both sides with polyethylene at a ratio of 15 g/m² per side, treating it with a corona discharge, and applying the following composition thereto at a ratio of 15² m/l:

| | |
|---|---|
| demineralized water | 750 ml |
| gelatin | 45 g |
| silver sulphide/nickel sulphide development nuclei | 7 g |
| 2% aqueous solution of density/tone-controlling compound saponin | 7.5 ml |
| | 10 g |
| | 5 g |

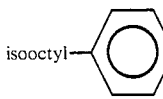

| | |
|---|---|
| 20% aqueous formaldehyde | 8.5 ml |
| demineralized water to make | 1000 ml |

After separation of the contacting elements the transmission density ($D_{TR}$), the saturation density ($D_S$), and the reflection density ($D_{RF}$) of the positive print were measured. Saturation density is the highest reflection density obtained in a DTR image of a step wedge. It is found in the areas of lower amounts of transferred silver.

The production of positive prints by means of the above described elements and processing solution according to the DTR-process was repeated several times in the same way except that the density- and tone-controlling compound was modified as indicated in the following Table 2. The term blank means that in that particular case no density- and tone-controlling compound was present in the image-receiving layer. Compound A is a comparison compound, which has been described in U.S. Pat. No. 3,053,657 and corresponds to the formula:

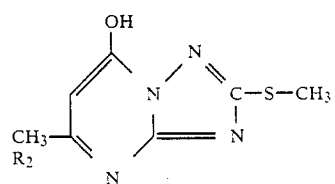

TABLE 2

| Density- and tone-controlling compound | ($D_{TR}$) | ($D_S$) | ($D_{RF}$) | Concentration in mol per m² |
|---|---|---|---|---|
| Blank | 3.21 | 1.74 | 1.55 | — |
| Compound A | 3.07 | 1.75 | 1.58 | $76.5 \times 10^{-6}$ |
| Compound 2 | 3.14 | 1.95 | 1.75 | $71.4 \times 10^{-6}$ |
| Compound 9 | 2.83 | 1.77 | 1.62 | $66.9 \times 10^{-6}$ |
| Compound 15 | 3.06 | 1.94 | 1.78 | $76.5 \times 10^{-6}$ |
| Compound 21 | 2.91 | 1.87 | 1.70 | $58.5 \times 10^{-6}$ |

The results listed in Table 2 show that the reflection density ($D_{RF}$) measured on the positive prints obtained with density- and tone-controlling compounds 2, 9, 15, and 21 according to the present invention is higher than that of the blank and of the comparison compound A. The transmission densities ($D_{TR}$) are not substantially decreased. The saturation density ($D_S$) of compounds 2, 9, 15, and 21 is higher than that of the blank and of the comparison compound A.

EXAMPLE 2

Photosensitive elements were exposed image-wise and moistened with a processing solution, as described in Example 1.

The moistened photosensitive elements were brought in contact for 8 s with non-light-sensitive elements prepared by coating polyethylene-covered paper support as described in Example 1 with the following composition at a ratio of 1 l per 23.5 m²:

| | |
|---|---|
| demineralized water | 925 ml |
| gelatin | 47 g |
| silver sulphide/nickel sulphide development nuclei | 16.5 g |
| saponin | 2 g |
| density- and tone-controlling compound | $7 \times 10^{-5}$ mol/m² |

While still wet the resulting layer was coated with the following composition at a ratio of 1 l per 66 m²:

| | |
|---|---|
| demineralized water | 964 ml |
| gelatin | 20 g |
| 20% aqueous formaldehyde | 8.5 ml |
| 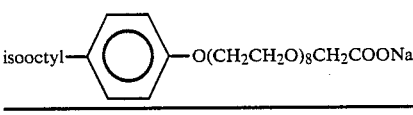 | 12 g |

After separation of the contacting elements ($D_{TR}$), ($D_S$), and ($D_{RF}$) of the positive prints were measured.

The production of positive prints according to the DTR-process was repeated several times in the same way except that the density- and tone-controlling compound was modified as indicated in the following Table 3.

TABLE 3

| Density- and tone-controlling compound | ($D_{TR}$) | ($D_S$) | ($D_{RF}$) | Tone |
|---|---|---|---|---|
| Blank | 3.09 | 1.64 | 1.54 | brownish black |
| Compound A | 3.10 | 1.70 | 1.60 | brownish black |
| Compound 2 | 3.10 | 1.84 | 1.70 | black |
| Compound 6 | 2.61 | 1.74 | 1.64 | black |
| Compound 9 | 2.75 | 1.74 | 1.67 | black |
| Compound 21 | 2.82 | 1.92 | 1.80 | black |

The results listed in Table 3 show that the reflection density ($D_{RF}$) measured on the positive prints obtained with density- and tone-controlling compounds 2, 6, 9, and 21 according to the present invention is higher than that of the blank and of the comparison compound A. The transmission densities ($D_{TR}$) are not substantially decreased. The saturation density ($D_S$) of compounds 2, 6, 9, and 21 is higher than that of the blank and of the comparison compound A.

The tone of the positive images obtained with the blank and with comparison compound A is brownish black, which suggests that light impinging thereon is scattered at the very surface of the images and thus gives rise to an unpleasant bronzing effect. In contrast, the tone of the positive images obtained with compounds 2, 6, 9, and 21 is a pleasant neutral black in consequence of the scattering of incident light on image particles that lie deeper into the positive image.

EXAMPLE 3

Photosensitive elements were exposed image-wise and moistened with a processing solution, as described in Example 1.

The moistened photosensitive elements were brought in contact for 30 s with non-light-sensitive elements prepared by coating polyethylene-covered paper support as described in Example 1 with the following composition at a ratio of 1 l per 28.6 m²:

| | |
|---|---|
| gelatin | 34.7 g |
| silver sulphide/nickel sulphide development nuclei | 22.9 g |
| sodium isotetradecyl sulphate | 2 g |
| 20% aqueous formaldehyde | 3.7 ml |
| density- and tone-controlling compound | 40 mg/m² |
| succinimide | (*) |
| demineralized water in an amount sufficient to make | 1 l | and coating the resulting image-receiving layer while still wet with the following composition for an antistress layer at a ratio of 1 l per 50 m²:

| | |
|---|---|
| gelatin | 0.7 g/m² |
| 20% aqueous formaldehyde | 3.5 ml |
| sodium isotetradecyl sulphate | 10 g |
| perfluorocaprylic acid | 2 g |
| aqueous dispersion of SiO₂ | (*) |
| mixture consisting of 855 ml of aqueous dispersion (30% solids) of SiO₂ and 145 ml of 1 part of epoxysilane having the structural formula VIII given above and 19 parts of ethanol | (*) |
| demineralized water in an amount sufficient to make | 1 l |

(*) means that the amount is shown in Table 4 hereinafter.

After separation of the contacting elements, the values for ($D_{TR}$) and ($D_{RF}$) of the transfer images were measured and the colour of the light viewed in transmission through the transfer images was evaluated.

The production of transfer images by means of the above described elements and processing solution according to the DTR-process was repeated several times in the same way, except that (1) the nature of the density- and tone-controlling compound differed as shown in the following Table 4 and that (2) the amount of succinimide, the amount of aqueous dispersion of SiO₂, and the amount of the SiO₂/epoxysilane combination were as shown in Table 4. The term blank means that in that particular case no density- and tone-controlling compound, no succinimide, no aqueous dispersion of SiO₂, nor the SiO₂/epoxysilane combination were present in the image-receiving layer and the antistress layer.

TABLE 4

| Non-light-sensitive Element comprising | ($D_{TR}$) | ($D_{RF}$) | Transmitted tone |
|---|---|---|---|
| Blank — | 3.45 | 1.74 | red |
| +Compd.6 | 2.87 | 1.77 | neutral grey |
| +Compd.6 + 10 mg/m2 succinimide | 3.21 | 1.78 | neutral grey |
| +Compd.6 + SiO$_2$(⅓rd of the gelatin) | 2.84 | 1.88 | neutral grey |
| +Compd.6 + 39 mg SiO$_2$/epoxysilane mixt. | 3.88 | 1.83 | neutral grey |
| +Compd.9 | 3.60 | 1.79 | neutral grey |
| +Compd.9 + 100 mg/m2 succinimide | 3.74 | 1.95 | neutral grey |
| +Compd.9 + SiO$_2$(⅓rd of the gelatin) | 3.31 | 1.91 | neutral grey |
| +Compd.9 + 39 mg SiO$_2$/epoxysilane mixt. | 3.37 | 1.86 | neutral grey |
| +Compd.15 | 2.93 | 1.84 | neutral grey |
| +Compd.15 + 10 mg/m2 succinimide | 3.27 | 1.88 | neutral grey |
| +Compd.15 + SiO$_2$(⅓rd of the gelatin) | 3.08 | 1.96 | neutral grey |
| +Compd.21 | 2.88 | 1.76 | neutral grey |
| +Compd.21 + 100 mg/m2 succinimide | 3.55 | 1.80 | neutral grey |
| +Compd.21 + SiO$_2$(⅓rd of the gelatin) | 2.92 | 1.89 | neutral grey |
| +Compd.21 + 39 mg SiO$_2$/epoxysilane mixt. | 3.05 | 1.80 | neutral grey |

In Table 4 the values listed for ($D_{TR}$) have been obtained after deduction of 0.66 for the density of the paper support.

The results listed in Table 4 show that the reflection density ($D_{RF}$) measured on the transfer images obtained with density- and tone-controlling compounds 6, 9, 15, and 21 according to the present invention is higher than that of the blank. The supplemental presence of succinimide in the image-receiving layer or of aqueous dispersion of SiO$_2$ or mixture of SiO$_2$ and epoxysilane in the antistress layer gave an even higher increase of the reflection density ($D_{RF}$). The transmission densities ($D_{TR}$) are not substantially decreased.

The tone of the transfer image obtained with the blank is red to reddsh brown, which suggests that light impinging thereon is scattered at the very surface of the images and thus gives rise to an unpleasant toning effect. In contrast, the tone of the transfer images obtained with compounds 6, 9, 15, and 21 is a pleasant neutral grey in consequence of the scattering of incident light on image particles that lie deeper in the transfer image.

We claim:

1. Method of making a DTR-image comprising the steps of image-wise exposing a photosensitive element comprising a photographic silver halide emulsion layer, developing the exposed emulsion layer with the aid of an alkaline processing solution in the presence of a silver halide solvent and contacting said photosensitive element with a non-photosensitive element to cause silver complexes to diffuse from the emulsion layer into an image-receiving layer of said non-photosensitive element thereby to form a silver transfer image in that layer through the presence of development nuclei in that layer, wherein said image-receiving layer or a hydrophilic colloid layer in water-permeable relationship therewith contains before the said contacting and transfer image formation a 7-hydroxy-s-triazolo-[1,5-a]-pyrimidine corresponding to the following general formula (I):

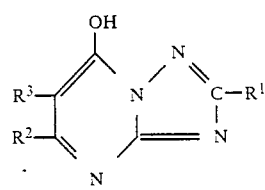

wherein:
each of $R^1$, $R^2$, and $R^3$, which may be the same or different, is one selected from the group consisting of:
(a) hydrogen,
(b) a $C_1$-$C_8$alkyl group, and
(c) an Alk$_1$—X—Alk$_2$—Y— group, wherein
Alk$_1$ represents a $C_1$-$C_8$alkyl group or substituted $C_1$—$C_8$alkyl group,
X represents —O— or —S—,
Alk$_2$ represents a $C_1$—$C_8$alkylene group or a substituted $C_1$—$C_8$alkylene group, and
Y is one selected from the group consisting of a single bond, —O—, —S—, —CONH—, —SO$_2$NH—, and —NHCONH—, or wherein:
each of $R^1$ and $R^2$ (the same or different) represents hydrogen or a said group (b) or (c) and $R^3$ represents a $C_1$-$C_8$alkylthio group or a $C_1$-$C_8$alkylthio group having a substituted $C_1$-$C_8$alkyl group,
at least one of $R^1$, $R^2$, and $R^3$, however, being other than hydrogen and other than $C_1$-$C_8$alkyl.

2. Non-light-sensitive element for the formation therein of a transfer image according to the DTR-process comprising an image-receiving layer containing a development nuclei wherein the said image-receiving layer or a hydrophilic colloid lalyer in water-permeable relationship therewith comprises before the said transfer image formation a 7-hydroxy-s-triazolo-[1,5-a]-pyrimidine corresponding to the following general formula (I):

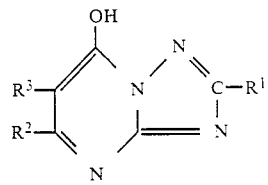

wherein:
each of $R^1$, $R^2$, and $R^3$, which may be the same or different, is one selected from the group consisting of:
(a) hydrogen,
(b) a $C_1$-$C_8$alkyl group, and
(c) an $Alk_1$—X—$Alk_2$—Y— group, wherein
$Alk_1$ represents a $C_1$-$C_8$alkyl group or a substituted $C_1$-$C_8$alkyl group,
X represents —O— or —S—,
$Alk_2$ represents a $C_1$-$C_8$alkylene group or a substituted $C_1$-$C_8$alkylene group, and
Y is one selected from the group consisting of a single bond, —O—, —S—, —CONH—, —$SO_2$NH—, and —NHCONH—,
or wherein:
each of $R^1$ and $R^2$ (the same or different) represents hydrogen or a said group (b) or (c) and $R^3$ represents a $C_1$-$C_8$alkylthio group or a $C_1$—$C_8$alkylthio group having a substituted $C_1$—$C_8$alkyl group,
at least one of $R^1$, $R^2$, and $R^3$, however, being other than hydrogen and other than $C_1$—$C_8$alkyl.

3. A non-light-sensitive element according to claim 2, wherein said 7-hydroxy-s-triazolo-[1,5-a]-pyrmidine is present in said image-receiving layer in an amount ranging ranging from 10 mg to 100 mg per m².

4. A non-light-sensitive element according to claim 2, wherein said image-receiving layer and/or said non-light-sensitive hydrophilic colloid layer in water-permeable relationship therewith also comprises at least one of the group consisting of the combination of colloidal silica and an epoxysilane, a dihydroxybenzene, and succinimide.

5. A non-light-sensitive element according to claim 4, wherein said image-receiving layer comprises succinimide and said non-light-sensitive hydrophillic colloid layer in water-permeable relationship with said image-receiving layer comprises colloidal silica and/or the combination of colloidal silica and an epoxysilane.

6. A non-light-sensitive element according to claim 4, wherein said epoxysilane corresponds to the structural formula VIII:

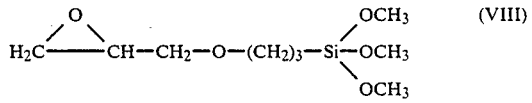

7. A non-light-sensitive element according to claim 2, wherein said image-receiving layer comprises silver nickel sulphide development nuclei.

* * * * *